(12) United States Patent
Reimers

(10) Patent No.: US 11,553,976 B2
(45) Date of Patent: Jan. 17, 2023

(54) FLEXIBLE BRACKET SYSTEM FOR MEDICAL APPARATUSES

(71) Applicant: Drägerwerk AG & Co. KGaA, Lübeck (DE)

(72) Inventor: Hans-Karsten Reimers, Hamberge (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 15/883,435

(22) Filed: Jan. 30, 2018

(65) Prior Publication Data

US 2018/0213932 A1 Aug. 2, 2018

(30) Foreign Application Priority Data

Jan. 31, 2017 (DE) ...................... 10 2017 000 851.5

(51) Int. Cl.
| | |
|---|---|
| *A61B 50/10* | (2016.01) |
| *A47B 57/04* | (2006.01) |
| *A47B 57/42* | (2006.01) |
| *A47B 96/06* | (2006.01) |
| *A47F 5/08* | (2006.01) |

(Continued)

(52) U.S. Cl.
CPC ............ *A61B 50/10* (2016.02); *A47B 57/045* (2013.01); *A47B 57/42* (2013.01); *A47B 96/067* (2013.01); *A47F 5/0838* (2013.01); *A61G 13/10* (2013.01); *A47B 57/58* (2013.01); *A61G 13/101* (2013.01)

(58) Field of Classification Search
CPC ..... A47B 96/067; A47B 57/42; A47B 96/061; A47B 57/52; A47B 57/045; A47B 47/022; A47B 57/58; F16M 13/02; A61M 5/1413; A61M 5/1415; A61M 2209/08; A61M 2209/082; A61G 7/0503; A61G 5/10; A61G 12/008; A61G 13/101; A61G 13/12; A61G 2203/80; A61G 13/129; A61G 13/10; A61G 13/1235; A61B 50/33; A61B 50/13; A61B 50/10
USPC ................... 248/235, 242; 211/193; 108/108
See application file for complete search history.

(56) References Cited

U.S. PATENT DOCUMENTS

| | | | | |
|---|---|---|---|---|
| 224,863 | A | * | 2/1880 | Blessing .............. A47B 96/061 248/241 |
| 945,280 | A | * | 1/1910 | Lindberg ............. A47B 57/045 108/10 |

(Continued)

FOREIGN PATENT DOCUMENTS

| | | |
|---|---|---|
| CN | 205568369 U | 9/2016 |
| DE | 376490 C * | 5/1923 ............. A61B 50/10 |

(Continued)

OTHER PUBLICATIONS

US 5,727,745 A, 03/1998, Vara (withdrawn)*

*Primary Examiner* — Jonathan Liu
*Assistant Examiner* — Taylor Morris
(74) *Attorney, Agent, or Firm* — McGlew and Tuttle, P.C.

(57) ABSTRACT

A support device (10) forms a medical apparatuses bracket system and functions as a bracket system for medical apparatuses (12). The support device (10) includes a central vertical, or at least essentially vertical, column (14) and at least one tine (20) and optionally two or more tines (20). The tine (20) or tines (20) is/are oriented obliquely to a cross-beam (22) mounted on the column (14).

18 Claims, 4 Drawing Sheets

(51) Int. Cl.
*A61G 13/10* (2006.01)
*A47B 57/58* (2006.01)

(56) References Cited

U.S. PATENT DOCUMENTS

| | | | | |
|---|---|---|---|---|
| 1,062,901 A * | 5/1913 | Entwhistle | ............ | A47B 57/42 248/243 |
| 2,503,375 A * | 4/1950 | Burg | ............ | A47G 25/746 211/104 |
| 2,642,250 A * | 6/1953 | Kasnowich | ............ | A61G 13/12 248/214 |
| 2,665,869 A * | 1/1954 | Samuels | ............ | A47F 5/0838 211/59.1 |
| 3,114,531 A * | 12/1963 | Weber | ............ | A47B 57/045 248/242 |
| 3,252,678 A * | 5/1966 | Lasch | ............ | A47F 5/06 211/123 |
| 3,337,880 A * | 8/1967 | Florek | ............ | A61M 5/1415 5/503.1 |
| 3,410,268 A * | 11/1968 | Lencci | ............ | A61M 3/022 604/31 |
| 3,476,256 A * | 11/1969 | Roger | ............ | A61G 13/10 248/173 |
| 3,548,827 A * | 12/1970 | Abel | ............ | A61G 7/0503 604/318 |
| 3,653,624 A * | 4/1972 | Abel | ............ | A61G 9/00 248/312 |
| 3,674,230 A * | 7/1972 | Propst | ............ | A47B 57/42 248/188.8 |
| 3,794,183 A * | 2/1974 | Colbridge | ............ | A47B 46/00 211/208 |
| 3,823,709 A * | 7/1974 | McGuire | ............ | A61B 17/0293 128/850 |
| 3,858,827 A * | 1/1975 | Glassbrook | ............ | B65H 49/04 242/154 |
| 3,907,119 A * | 9/1975 | Franz | ............ | A47F 5/10 211/196 |
| 3,957,240 A * | 5/1976 | Johansson | ............ | B63C 5/02 248/214 |
| 4,037,729 A * | 7/1977 | DeSisto | ............ | A47F 5/103 211/208 |
| 4,059,248 A * | 11/1977 | Kuntz | ............ | A47H 27/00 248/214 |
| 4,316,547 A * | 2/1982 | Varon | ............ | A47G 25/0692 211/105.1 |
| 4,318,486 A * | 3/1982 | Bobrowski | ............ | A47F 5/0876 211/87.01 |
| 4,367,819 A * | 1/1983 | Lewis | ............ | A47G 25/0678 211/106.01 |
| 4,376,521 A * | 3/1983 | Walters | ............ | A47K 1/08 108/152 |
| 4,449,686 A * | 5/1984 | Kersey | ............ | A47F 7/24 248/215 |
| 4,454,870 A * | 6/1984 | Schwentker | ............ | A61F 5/3707 128/869 |
| 4,467,925 A * | 8/1984 | Ratzloff | ............ | B25H 3/04 211/103 |
| 4,474,299 A * | 10/1984 | Andrews | ............ | A47F 7/24 211/123 |
| 4,498,693 A * | 2/1985 | Schindele | ............ | A61G 13/107 248/223.41 |
| 4,548,378 A * | 10/1985 | Worrallo | ............ | A47B 57/56 248/242 |
| 4,549,712 A * | 10/1985 | Simon | ............ | A47B 57/42 248/224.8 |
| 4,583,648 A * | 4/1986 | Buffington | ............ | A47B 57/045 211/106 |
| 4,624,245 A * | 11/1986 | Mullin | ............ | A61G 13/12 5/621 |
| 4,634,010 A * | 1/1987 | Otema | ............ | A47F 7/24 211/103 |
| 4,635,914 A * | 1/1987 | Kabanek | ............ | A61G 13/12 5/601 |
| 4,648,144 A * | 3/1987 | Rose | ............ | A61G 7/05 248/214 |
| 4,723,663 A * | 2/1988 | Learn | ............ | A47F 5/0823 211/59.2 |
| 4,807,659 A * | 2/1989 | Schindele | ............ | F16L 3/01 137/271 |
| 4,809,941 A * | 3/1989 | Sheridan | ............ | A47B 96/061 248/235 |
| 4,842,230 A * | 6/1989 | Cobb | ............ | A47F 5/083 211/106 |
| 4,854,535 A * | 8/1989 | Winter | ............ | A47B 57/42 248/220.22 |
| 4,869,378 A * | 9/1989 | Miller | ............ | A47F 5/0853 211/94.01 |
| 4,895,331 A * | 1/1990 | Nehls | ............ | A47B 57/565 108/108 |
| 4,970,900 A * | 11/1990 | Shepherd | ............ | A61B 5/0215 600/488 |
| 5,000,407 A * | 3/1991 | Juji | ............ | A61M 1/3646 248/125.8 |
| 5,116,007 A * | 5/1992 | Von Gunton | ............ | A47B 57/42 108/108 |
| 5,152,404 A * | 10/1992 | Salrin | ............ | A47F 5/0807 211/46 |
| 5,160,106 A * | 11/1992 | Monick | ............ | A61G 7/0503 248/231.71 |
| 5,185,971 A * | 2/1993 | Johnson, Jr. | ............ | A47B 57/408 211/94.01 |
| 5,224,609 A * | 7/1993 | Bauer | ............ | A47F 5/0838 211/65 |
| 5,236,162 A * | 8/1993 | Desjardins | ............ | A61M 5/1415 248/214 |
| 5,287,575 A * | 2/1994 | Allen | ............ | A61G 13/101 248/231.41 |
| 5,319,816 A * | 6/1994 | Ruehl | ............ | A61G 7/0503 211/86.01 |
| 5,332,108 A * | 7/1994 | Blass | ............ | A47B 96/067 211/103 |
| 5,358,205 A * | 10/1994 | Starkey | ............ | F16B 7/0493 248/220.21 |
| 5,390,383 A * | 2/1995 | Carn | ............ | A61G 13/12 128/877 |
| 5,439,120 A * | 8/1995 | Brozak | ............ | A47F 5/0838 206/806 |
| 5,452,875 A * | 9/1995 | Kern | ............ | A47B 57/045 108/108 |
| 5,472,103 A * | 12/1995 | Merl | ............ | A47B 47/022 211/187 |
| 5,472,167 A * | 12/1995 | Shillington | ............ | A47F 5/0853 211/94.01 |
| 5,509,541 A * | 4/1996 | Merl | ............ | A47B 45/00 211/103 |
| 5,564,658 A * | 10/1996 | Rinderer | ............ | F16L 3/22 248/49 |
| 5,582,376 A * | 12/1996 | Thompson | ............ | A47B 96/067 211/94.01 |
| 5,588,166 A * | 12/1996 | Burnett | ............ | A61G 7/05 248/214 |
| 5,687,856 A * | 11/1997 | Kendrena | ............ | A47F 5/0846 211/65 |
| 5,695,078 A * | 12/1997 | Otema | ............ | A47B 57/045 108/108 |
| 5,738,019 A * | 4/1998 | Parker | ............ | A47B 46/00 108/108 |
| 5,738,319 A * | 4/1998 | Grassi | ............ | A47G 7/044 248/215 |
| 5,740,927 A * | 4/1998 | Yemini | ............ | A47B 96/067 211/66 |
| 5,758,374 A * | 6/1998 | Ronci | ............ | A61G 13/101 108/152 |
| 5,769,247 A * | 6/1998 | Merl | ............ | A47B 47/022 211/103 |
| 5,794,795 A * | 8/1998 | Stemmons | ............ | H02B 1/01 211/191 |
| 5,806,822 A * | 9/1998 | Schulz | ............ | A61B 90/50 211/70.6 |

(56) References Cited

U.S. PATENT DOCUMENTS

| | | | | |
|---|---|---|---|---|
| 5,857,577 A * | 1/1999 | Thomas | A47B 57/26 | 211/94.01 |
| 5,871,187 A * | 2/1999 | Pihlaja | A47B 57/42 | 248/214 |
| 5,871,189 A * | 2/1999 | Hoftman | A61G 7/0503 | 248/229.16 |
| 5,898,961 A * | 5/1999 | Ambach | A61G 7/05 | 292/108 |
| 5,909,733 A * | 6/1999 | Ehrich | A61G 7/075 | 128/869 |
| 5,940,904 A * | 8/1999 | Lutz | A61H 33/6026 | 4/541.3 |
| 5,975,469 A * | 11/1999 | Chen | G06F 3/0395 | 248/118.1 |
| 6,050,426 A * | 4/2000 | Leurdijk | A47B 96/067 | 211/57.1 |
| 6,076,208 A * | 6/2000 | Heimbrock | A61G 1/0287 | 5/183 |
| 6,142,433 A * | 11/2000 | Winger | A47B 96/061 | 248/214 |
| 6,145,677 A * | 11/2000 | Corniel | A47G 25/0692 | 211/105.1 |
| 6,195,820 B1 * | 3/2001 | Heimbrock | A61G 13/12 | 403/68 |
| 6,213,481 B1 * | 4/2001 | Marchese | A61G 12/001 | 248/282.1 |
| 6,237,799 B1 * | 5/2001 | Emerson | A47B 23/025 | 220/476 |
| 6,253,399 B1 * | 7/2001 | Wagner | A47B 23/025 | 108/49 |
| 6,299,001 B1 * | 10/2001 | Frolov | A47F 5/01 | 211/106 |
| 6,302,280 B1 * | 10/2001 | Bermes | B60R 9/00 | 211/175 |
| 6,305,557 B1 * | 10/2001 | Brooks | B25H 3/04 | 211/70.6 |
| 6,364,141 B1 * | 4/2002 | Ehrgott | A47F 5/0823 | 211/103 |
| 6,378,255 B1 * | 4/2002 | Eich | A47B 21/00 | 40/605 |
| 6,378,828 B1 * | 4/2002 | Valiulis | A47F 5/0838 | 211/59.1 |
| 6,407,335 B1 * | 6/2002 | Franklin-Lees | A61M 5/1413 | 174/50 |
| 6,409,131 B1 * | 6/2002 | Bentley | A01K 97/10 | 248/219.4 |
| 6,467,743 B1 * | 10/2002 | Shiojima | A47F 5/0838 | 211/94.01 |
| 6,484,332 B2 * | 11/2002 | Korver, II | A61G 7/1017 | 5/624 |
| 6,536,699 B2 * | 3/2003 | Glass | B65H 75/4476 | 242/400.1 |
| 6,540,093 B1 * | 4/2003 | Shumway | A47B 57/30 | 108/147.11 |
| 6,543,627 B1 * | 4/2003 | Schiavo | A47B 96/025 | 211/26 |
| 6,561,474 B1 * | 5/2003 | Walter | A47F 5/0815 | 211/94.01 |
| 6,575,315 B2 * | 6/2003 | Zidek | A47F 5/01 | 211/106 |
| 6,622,980 B2 * | 9/2003 | Boucher | F16B 7/0493 | 248/231.51 |
| 6,626,445 B2 * | 9/2003 | Murphy | A61G 12/001 | 280/47.34 |
| 6,675,980 B2 * | 1/2004 | Ehrgott | A47F 5/0823 | 211/189 |
| 6,758,355 B2 * | 7/2004 | Zidek | A47F 5/06 | 211/90.03 |
| 6,758,448 B1 * | 7/2004 | Williams | A47B 96/02 | 248/125.1 |
| 6,850,208 B1 * | 2/2005 | Ferrante | G06Q 10/087 | 345/1.1 |
| 6,932,225 B2 * | 8/2005 | Rowe | A47B 57/30 | 211/90.02 |
| 6,935,523 B2 * | 8/2005 | Ahn | A47F 5/137 | 211/189 |
| 6,964,399 B1 * | 11/2005 | O'Neill | F16M 11/10 | 248/292.13 |
| 7,140,500 B2 * | 11/2006 | McCoy | H02G 3/30 | 211/60.1 |
| 7,140,572 B2 * | 11/2006 | Glass | B65H 75/4476 | 242/400.1 |
| 7,314,144 B2 * | 1/2008 | Stitchick | A47B 47/022 | 211/125 |
| 7,369,401 B1 * | 5/2008 | Floersch | F16M 11/08 | 292/301 |
| 7,398,951 B1 * | 7/2008 | Sugalski | A61G 7/0503 | 248/214 |
| 7,422,431 B2 * | 9/2008 | White | A61C 19/00 | 433/77 |
| 7,438,268 B2 * | 10/2008 | Kologe | A47F 5/0838 | 248/220.22 |
| 7,516,924 B2 * | 4/2009 | White | A61B 90/50 | 248/123.11 |
| 7,562,883 B2 * | 7/2009 | Livengood | A61G 12/001 | 280/43.17 |
| 7,641,158 B2 * | 1/2010 | Ferguson | A61M 5/1415 | 248/157 |
| 7,641,356 B2 * | 1/2010 | Pieroth | F21L 15/10 | 248/214 |
| 7,665,606 B2 * | 2/2010 | Gaillard | A61B 46/10 | 206/363 |
| 7,770,855 B2 * | 8/2010 | Locke | A61M 1/0025 | 248/230.2 |
| 7,798,339 B2 * | 9/2010 | Brooks | G11B 33/02 | 211/103 |
| 7,882,583 B2 * | 2/2011 | Skripps | A61G 13/101 | 5/621 |
| 7,922,132 B2 * | 4/2011 | Saez | F16M 11/041 | 248/124.1 |
| 7,967,137 B2 * | 6/2011 | Fulbrook | A61B 90/57 | 206/370 |
| 7,971,841 B2 * | 7/2011 | Van Wyk | A47B 81/00 | 211/123 |
| 8,074,815 B2 * | 12/2011 | Gerstner | A61B 50/20 | 211/193 |
| 8,079,311 B2 * | 12/2011 | Whalen | F16M 13/02 | 108/42 |
| 8,087,521 B2 * | 1/2012 | Schwartzkopf | A47B 96/061 | 211/103 |
| 8,182,056 B2 * | 5/2012 | Gossens | A47B 88/483 | 312/408 |
| 8,186,521 B2 * | 5/2012 | Yu | A47B 55/02 | 211/106 |
| 8,246,028 B2 * | 8/2012 | Larkin | A61M 5/1414 | 248/229.1 |
| 8,268,432 B2 * | 9/2012 | Malcolm | A61G 13/12 | 428/53 |
| 8,276,862 B2 * | 10/2012 | Eshita | F16M 11/10 | 248/160 |
| 8,333,038 B2 * | 12/2012 | Bates | A47B 95/008 | 52/36.6 |
| 8,336,839 B2 * | 12/2012 | Boccoleri | A61G 12/004 | 248/276.1 |
| 8,397,323 B2 * | 3/2013 | Skripps | A61B 6/0421 | 5/601 |
| 8,403,275 B2 * | 3/2013 | Cote | A61M 5/1415 | 211/85.18 |
| 8,408,404 B2 * | 4/2013 | Miller | B25H 1/00 | 211/90.01 |
| 8,508,918 B2 * | 8/2013 | Dittmer | F16M 11/10 | 361/679.01 |
| 8,596,473 B2 * | 12/2013 | Newbould | A47K 1/09 | 211/88.01 |
| 8,596,599 B1 * | 12/2013 | Carson | B60R 11/0235 | 211/26 |
| 8,657,133 B2 * | 2/2014 | McGowan | A47B 47/00 | 211/189 |

(56) References Cited

U.S. PATENT DOCUMENTS

| | | | | |
|---|---|---|---|---|
| 8,720,702 B2* | 5/2014 | Nagel | A47B 96/027 | 211/59.3 |
| 8,789,712 B2* | 7/2014 | Johnson | A47F 5/0025 | 211/71.01 |
| 8,844,951 B2* | 9/2014 | De Jong | B62B 3/10 | 361/679.01 |
| 8,960,612 B2* | 2/2015 | McCoy | F16L 3/223 | 211/193 |
| 8,964,359 B2* | 2/2015 | Bauer | A61G 12/004 | 361/624 |
| 8,979,225 B2* | 3/2015 | Eckartsberg | A47B 57/42 | 312/408 |
| 8,998,009 B2* | 4/2015 | Kim | A47B 95/008 | 211/103 |
| 9,222,616 B2* | 12/2015 | Ergun | F16M 11/10 | |
| 9,468,312 B2* | 10/2016 | Denby | A47F 5/0043 | |
| 9,763,515 B2* | 9/2017 | Fratilla | A47B 73/00 | |
| 9,795,346 B2* | 10/2017 | Wasson, Jr. | A61B 6/107 | |
| 9,918,568 B1* | 3/2018 | Blake | A47B 57/545 | |
| 10,363,190 B2* | 7/2019 | Elias | A61G 7/075 | |
| 11,013,574 B1* | 5/2021 | Gomez | A61B 46/20 | |
| 11,135,114 B2* | 10/2021 | Apantaku | A61G 13/10 | |
| 2001/0017340 A1* | 8/2001 | Cernosek | F16L 3/00 | 248/510 |
| 2004/0133979 A1* | 7/2004 | Newkirk | A61F 5/3761 | 5/624 |
| 2004/0222341 A1* | 11/2004 | Breda | A61M 5/1415 | 248/200 |
| 2004/0226903 A1* | 11/2004 | Wang | A47B 57/04 | 211/187 |
| 2005/0028282 A1* | 2/2005 | Tillander | A61G 13/12 | 5/624 |
| 2005/0077436 A1* | 4/2005 | Nelson | F16L 3/223 | 248/68.1 |
| 2005/0081865 A1* | 4/2005 | Hubert | A61G 13/0054 | 128/845 |
| 2005/0150850 A1* | 7/2005 | Stitchick | A47B 47/022 | 211/90.03 |
| 2005/0206107 A1* | 9/2005 | Schubert | A61G 12/001 | 280/79.11 |
| 2005/0236544 A1* | 10/2005 | Mancino | H05K 7/1447 | 248/304 |
| 2006/0059934 A1* | 3/2006 | Howington | A47B 57/045 | 62/256 |
| 2006/0278781 A1* | 12/2006 | Homra | A61M 16/00 | 248/220.21 |
| 2007/0012637 A1 | 1/2007 | Yu et al. | | |
| 2007/0092366 A1* | 4/2007 | Bose | B66F 9/082 | 414/607 |
| 2007/0136947 A1* | 6/2007 | Limpert | F16M 13/022 | 5/600 |
| 2008/0053931 A1* | 3/2008 | Newbould | A47B 96/067 | 211/88.01 |
| 2009/0050756 A1* | 2/2009 | Newkirk | A61G 7/0503 | 248/176.1 |
| 2009/0126113 A1* | 5/2009 | Hejkal | A61G 13/12 | 5/603 |
| 2009/0266952 A1* | 10/2009 | Phillips, Sr. | A47B 96/061 | 248/206.5 |
| 2010/0052274 A1* | 3/2010 | West | A61M 5/1417 | 280/47.24 |
| 2010/0126953 A1* | 5/2010 | Lin | A47B 96/06 | 211/134 |
| 2010/0219144 A1* | 9/2010 | Salmon | A47B 96/067 | 211/94.01 |
| 2011/0061606 A1* | 3/2011 | Sevadjian | A01K 13/00 | 119/756 |
| 2011/0101179 A1* | 5/2011 | Fritch | F16M 11/08 | 248/125.7 |
| 2011/0108682 A1* | 5/2011 | Boaz | A47B 81/00 | 248/99 |
| 2011/0226715 A1 | 9/2011 | Schwartzkopf et al. | | |
| 2012/0018602 A1* | 1/2012 | Cattaneo | A47B 95/008 | 248/222.11 |
| 2013/0146551 A1* | 6/2013 | Simpson | A47B 57/408 | 211/86.01 |
| 2013/0247299 A1* | 9/2013 | Schleitzer | A61G 13/101 | 5/658 |
| 2013/0277932 A1* | 10/2013 | De Jong | A61G 12/001 | 280/79.11 |
| 2014/0007408 A1* | 1/2014 | Nool | A61M 5/1418 | 29/525.01 |
| 2014/0209550 A1* | 7/2014 | Pryor | A61M 5/1417 | 211/85.13 |
| 2014/0238408 A1* | 8/2014 | Shepherd | A61G 13/101 | 128/845 |
| 2014/0263890 A1* | 9/2014 | McCarthy | F16M 11/10 | 248/205.1 |
| 2015/0053728 A1* | 2/2015 | Womble | A47F 5/0838 | 223/85 |
| 2015/0097097 A1* | 4/2015 | Early | A47G 25/0678 | 248/215 |
| 2015/0259004 A1* | 9/2015 | Sabo | B62B 3/02 | 280/79.3 |
| 2015/0290064 A1* | 10/2015 | Kreuzer | A61G 13/123 | 128/845 |
| 2016/0120303 A1* | 5/2016 | Constantino | F16M 11/42 | 108/28 |
| 2016/0228315 A1* | 8/2016 | Perlman | A61G 13/10 | |
| 2016/0287461 A1* | 10/2016 | Naughton | A61G 13/101 | |
| 2017/0143572 A1* | 5/2017 | Bergman | A61G 13/101 | |
| 2017/0181908 A1* | 6/2017 | Jackson | G16H 20/40 | |
| 2017/0273846 A1* | 9/2017 | Yancey | A61G 13/101 | |
| 2018/0035801 A1* | 2/2018 | Kunsch | A47B 96/067 | |
| 2019/0262206 A1* | 8/2019 | Yancey | A61G 13/1245 | |
| 2020/0135355 A1* | 4/2020 | Colling | A61B 6/107 | |

FOREIGN PATENT DOCUMENTS

| | | | | |
|---|---|---|---|---|
| DE | 102011055414 A1 * | 5/2013 | | A61B 50/10 |
| KR | 20100008790 U | 9/2010 | | |

* cited by examiner (State of the Art)

FLEXIBLE BRACKET SYSTEM FOR MEDICAL APPARATUSES

CROSS REFERENCE TO RELATED APPLICATIONS

This application claims the benefit of priority under 35 U.S.C. § 119 of German Application 10 2017 000 851.5, filed Jan. 31, 2017, the entire contents of which are incorporated herein by reference.

FIELD OF THE INVENTION

The present invention pertains to a flexible bracket system for medical apparatuses, for example, for medical apparatuses in the form of medical supply units.

BACKGROUND OF THE INVENTION

Such bracket systems are known per se and shelf spaces arranged above one another in a shelf-like manner are available for medical apparatuses or the like.

One drawback of the prior-art bracket systems is that their shelf spaces are often broader than required, so that an unfavorably increased space requirement results for the bracket system overall. The fact that a shelf space of a bracket system is too small for a medical apparatus to be placed on it likewise comes into consideration, so that this medical apparatus either cannot be placed into the bracket system at all or does not stand securely there. In addition, at least the surfaces of the shelf spaces require regular cleaning, so that large shelf spaces lead to an increased cleaning effort and too large shelf spaces lead to an unnecessarily high cleaning effort.

SUMMARY OF THE INVENTION

An object of the present invention is to provide a bracket system that avoids at least some of the drawbacks outlined above.

According to the present invention, this object is accomplished by means of a support device functioning as a bracket system for medical apparatuses. To this end, the support device comprises at least one tine and at least one crossbeam intended for mounting the tine on the column. The tine is oriented obliquely to the crossbeam mounted on the column. The support device comprises a central vertical or at least essentially vertical column.

One advantage of the present invention is that a tine is narrow in relation to its protruding length and accordingly only forms a small surface to be cleaned. A medical apparatus, for example, can be suspended on such a tine. In case of a tine having a profile corresponding to a standard profile for mounting medical apparatuses or medical devices, a medical apparatus, for example, one for administering an infusion (drip), may be mounted on the tine and the standard profile thereof. In case of mounting a plurality of tines on the same crossbeam, especially in case of mounting tines in pairs on one crossbeam, these tines define a shelf space for a medical apparatus and this medical apparatus can be placed securely in the support device functioning as a bracket system, when this bracket system is positioned, for example, with its support feet or the like over the tines. In case of tines mounted in pairs, the resulting shelf space can be adapted accurately to the needed space requirement for a respective medical apparatus by means of tines spaced apart in a corresponding manner.

Advantageous embodiments of the support device are described. These exemplary embodiments of the present invention is explained in more detail below on the basis of the drawing. Objects or components corresponding to one another are provided with the same reference numbers in all figures.

The exemplary embodiment or each exemplary embodiment is not to be understood as a limitation of the present invention. Rather, variations and modifications of the concrete support device are possible within the framework of the present disclosure, especially such variants and combinations, which, for example, can be inferred by the person skilled in the art with respect to accomplishing the object by a combination or modification of some of the features described in connection with the general or specific part of the specification as well as contained in the claims and/or in the drawings and lead to a novel support device by means of combinable features.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a schematic top view showing a support device with a shelf space formed by means of two parallel tines for a medical apparatus or the like;

DESCRIPTION OF THE PREFERRED EMBODIMENTS

Figure 1:
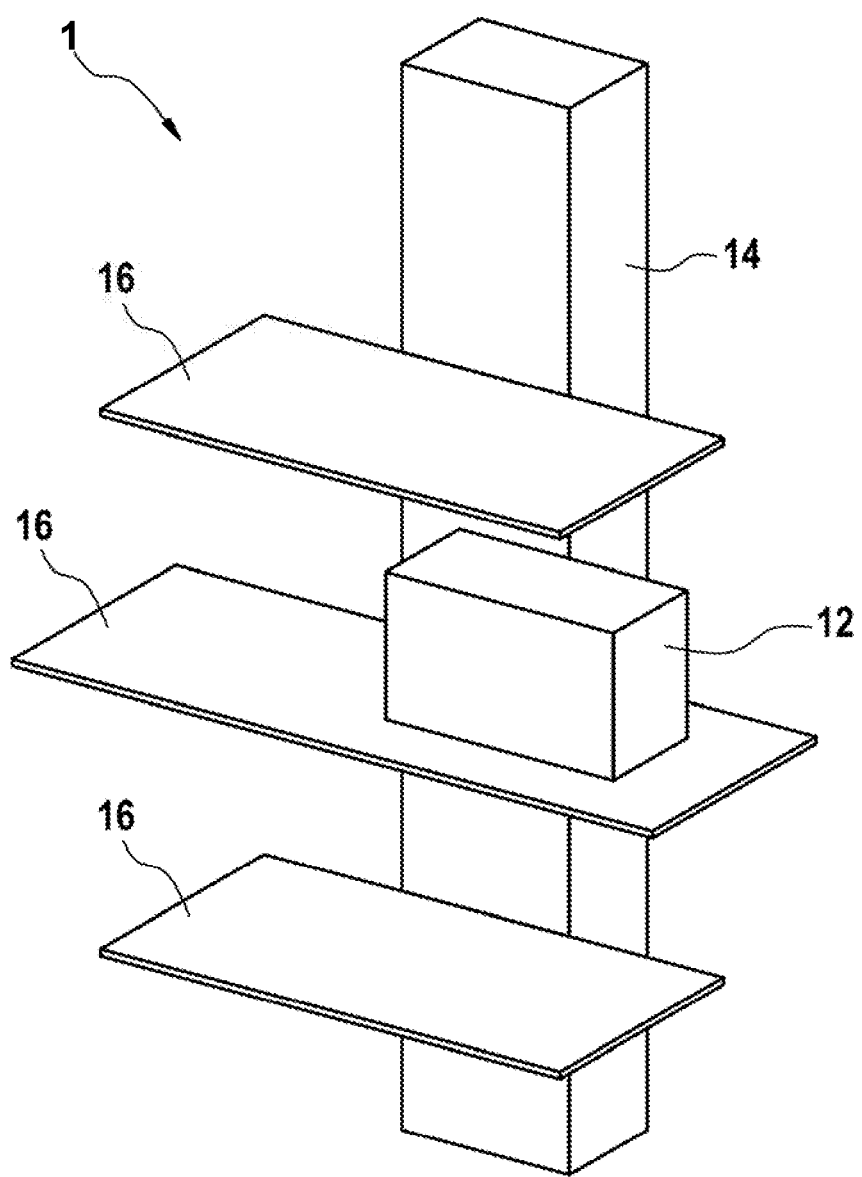
FIG. 1 is a schematic perspective view showing a support device for accommodating medical apparatuses, which is known per se, in principle.

Referring to the drawings, the view in FIG. 1 shows in a schematically simplified manner a support device 1, which is known per se, in principle, for example, for medical apparatuses 12 or the like. The support device 1 comprises a central vertical or at least essentially vertical column 14, forming, so to speak, the backbone of the support device 1, on which column 14 at least one shelf space 16, usually a plurality of shelf spaces 16 for medical apparatuses 12 or the like is or are mounted. The term "medical apparatus" 12 is used below as a generic term for apparatuses or equipment, which can be placed onto such a shelf space 16, without doing away with a more extensive generality. In this connection, the apparatus may be, for example, a monitor, a ventilator, an anesthesia apparatus, etc., and generally apparatuses as they are used in a hospital, especially in an operating room.

The column 14 of the support device 1 may be mounted (not shown), in principle, directly or indirectly on the ceiling, on the floor or on a side wall of a room, especially of an operating room or of a hospital room, in a building, usually in a hospital, in a manner known per se. The size of the shelf spaces 16 may vary and shelf spaces 16 with a corresponding area are mounted on the column 14 as needed.

As outlined in the introduction, such a support device 1 is not optimal because of the fixed size of each individual shelf space 16. A too large (too broad and/or too deep) shelf space 16 may lead to space problems in the area surrounding the support device 1. In case of a shelf space 16 that is too small for a medical apparatus 12 to be placed onto the support device 1, this shelf space 16 must be removed with corresponding expenditure of time and be replaced with a larger shelf space 16 before the apparatus 12 can be used. For complying with hygiene regulations, the entire surface of all shelf spaces 16 has to be cleaned, with corresponding expenditure of time and corresponding consumption of cleaning agents, regardless of the actual space requirement for medical apparatuses 12.

FIGS. 2 through 8 show, likewise in a schematically highly simplified manner, embodiments of a support device 10 provided in different configurations and shown in different views.

Figure 2:
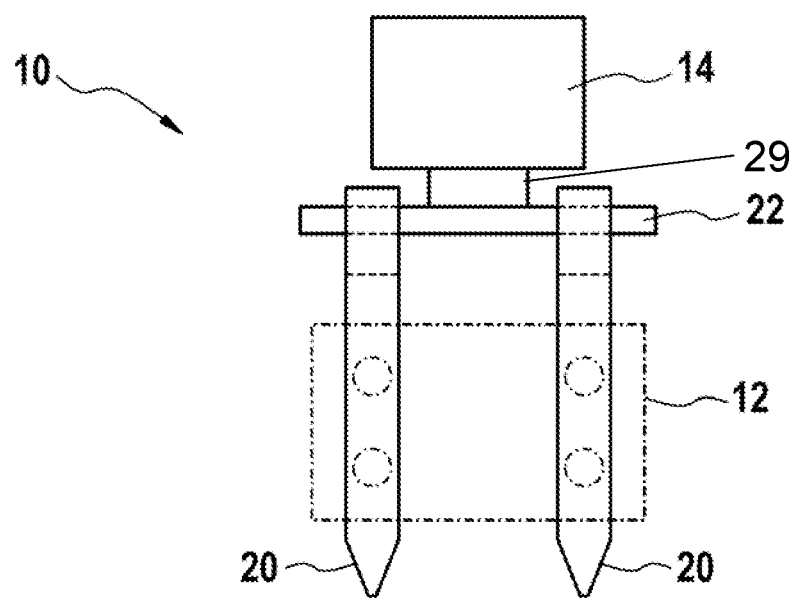

FIG. 2 shows a view of the support device 10 from above (with a view axis along the longitudinal axis of the column 14). It can be seen here that according to the central aspect of the innovation according to the invention one or more tines 20 come up to the location of a shelf space 16 mounted on the column. A medical apparatus 12, which is shown in phantom line in the view in FIG. 2 (as well as in FIGS. 4 and 5 described below), indicating a borderline thereof as well as support foot positions thereof. Each support foot is placed onto one of the tines 20, with the medical apparatus 12 put down onto these tines 20. The tines 20 function as support arms or cantilevers. The designation as tine 20 is borrowed from the corresponding designation of the fingers/tines of a forklift fork and is used below as a brief and handy designation for the support arms or cantilevers of the support device 10 according to the invention and as disclosed herein. As an alternative, the designation as support arm 20 or cantilever 20 may be used instead of the designation "tine" 20.

The tine or each tine 20 is connected to the column 14 via a crossbeam 22 mounted on the column 14. The crossbeam 22 is usually oriented horizontally. The tine or each tine 20 is oriented obliquely to the crossbeam 22 and two or more tines 20 mounted on a crossbeam 22 are usually aligned parallel to one another with their free ends.

Figure 3:
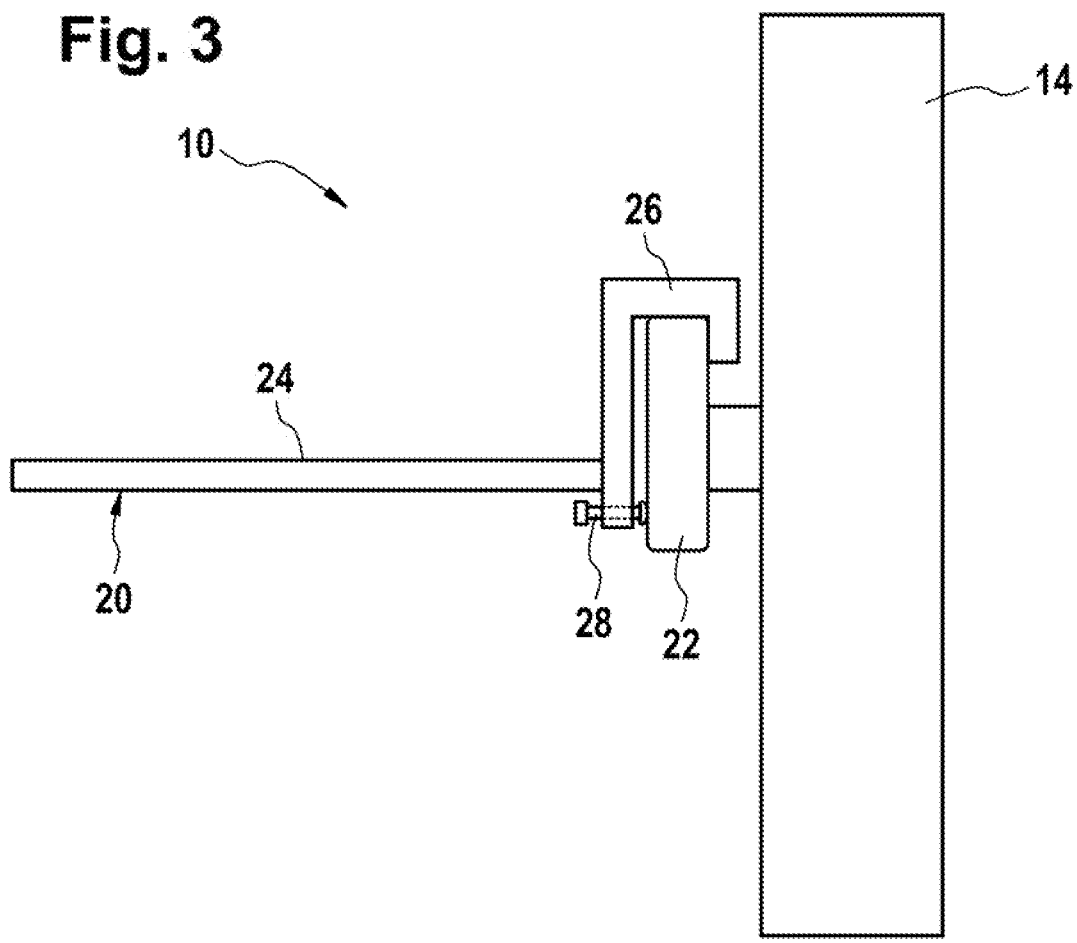
FIG. 3 is a lateral schematic view showing the support device according to FIG. 2.

The view in FIG. 3 shows the support device 10 in a lateral view. A possibility for mounting a tine 20 on the crossbeam 22 is shown here. Each tine 20 comprises a support section 24, which is usually oriented horizontally, and a connecting section intended for mounting on the crossbeam 22, which connecting section is configured in the embodiment described below as a suspended section 26, because the tine 20 with the suspended section 26 is placed onto the crossbeam 22 and the tine 20 is overall suspended with it on the crossbeam 22 in the embodiment shown in FIG. 3. The suspended section 26 comprises the top side of the crossbeam 22 in a hook-shaped manner and is supported indirectly or directly on the crossbeam 22 in connection with the hook-shaped section. In the embodiment being shown, the suspended section 26 is indirectly supported on the crossbeam 22, namely by means of an adjusting screw 28. The adjusting screw is an example of means for adjusting an inclination of the support section 24 of the tine 20 to the horizontal plane.

In the embodiment shown, the crossbeam 22 has a cuboid cross section and the largest longitudinal axis of the cross-sectional area is oriented vertically or at least essentially vertically in the state mounted on the column 14. The suspended section 26 is supported on the surface of the crossbeam 22 parallel with this longitudinal axis and facing away from the column 14. With the hook-shaped section, the suspended section 26 is supported on the surface parallel with the short longitudinal axis of the cross-sectional area. Here, the hook-shaped section also extends behind the crossbeam 22, i.e., in an area between the crossbeam 22 and the column 14, and hereby is in contact in at least some sections with the surface of the crossbeam 22 facing the column 14.

As an option, a position of the tine 20 or of each tine 20 on the crossbeam 22 in the axial direction of the crossbeam 22 can be adjusted. In this connection, the tine 20 or each tine 20 can preferably be freely positioned in the axial direction of the crossbeam 22, for example, by the tine 20 being moved with its suspended section 26 along the crossbeam 22. In this way, the position of the tine 20 on the support device 10 can be adjusted corresponding to the particular need. For example, a distance between two adjacent tines 20 mounted on a crossbeam 22 can be adjusted corresponding to an area of a medical apparatus 12 to be placed thereon and/or corresponding to a position of the support feet of this apparatus 12. Shelf spaces of a wide variety of medical apparatuses 12 can be created in this manner with the same tines 20 in each case. In addition, the position of medical apparatuses 12 placed on, for example, two tines 20 may also be adapted in relation to a central longitudinal axis of the column 14. It is thus possible, for example, to place a medical apparatus 12 centrally in front of the column 14 or laterally offset to the column 14. For example, an alternating arrangement of the medical apparatuses 12 along the height of the column 14 thus also come into consideration (each offset in relation to the column on the left side and on the right side) in case of a plurality of medical apparatuses 12 placed in the same support device 10.

In the case of a tine 20 with a suspended section 26 of the above-described kind, the tine 20 can be detachably connected to the crossbeam 22 and hence may, for example, be mounted on different crossbeams 22 when the support device 10 has a plurality of crossbeams 22 along the column 14. For example, a vertical position of a medical apparatus 12 to be placed in the support device 10 can be determined in this way. The possibility of detachably connecting a tine 20 to a crossbeam 22 is not limited to the above-described suspended section 26. In the same way, for example, provisions may be made for the tine 20 to be screwed to the crossbeam 22 for the detachable connection to this crossbeam 22 and/or be inserted into a recess in the crossbeam 22 and the like.

The detachable connectability of a tine 20 to a crossbeam 22 also allows the use of different tines 20, for example, tines 20 of different lengths and/or tines 20 with different load capacity, wherein for the latter the tines 20 are, for example, manufactured from different materials (plastic, metal, etc.) and/or have reinforcing structures.

As an option, at least one crossbeam 22 may also be detachably connected to the central column 14, for example, by means of screwing to the column 14, insertion into a recess in the column 14, etc. This allows the use of different crossbeams 22, for example, crossbeams 22 of different lengths and/or crossbeams 22 with different load capacity.

Figure 4:
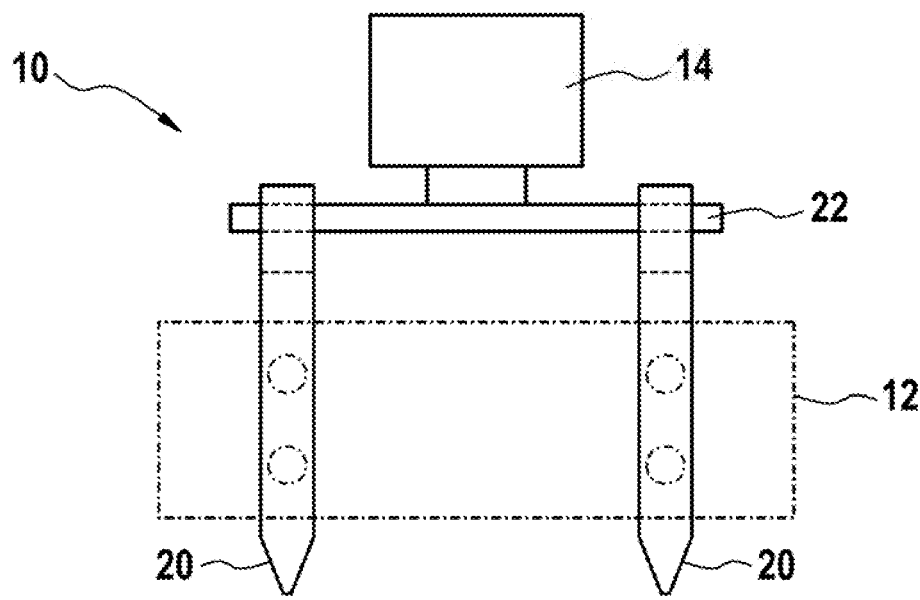
FIG. 4 is a top view showing a plane of the support device according to FIG. 2 with tines spaced apart at different distances in comparison to FIG. 2.
Figure 5:
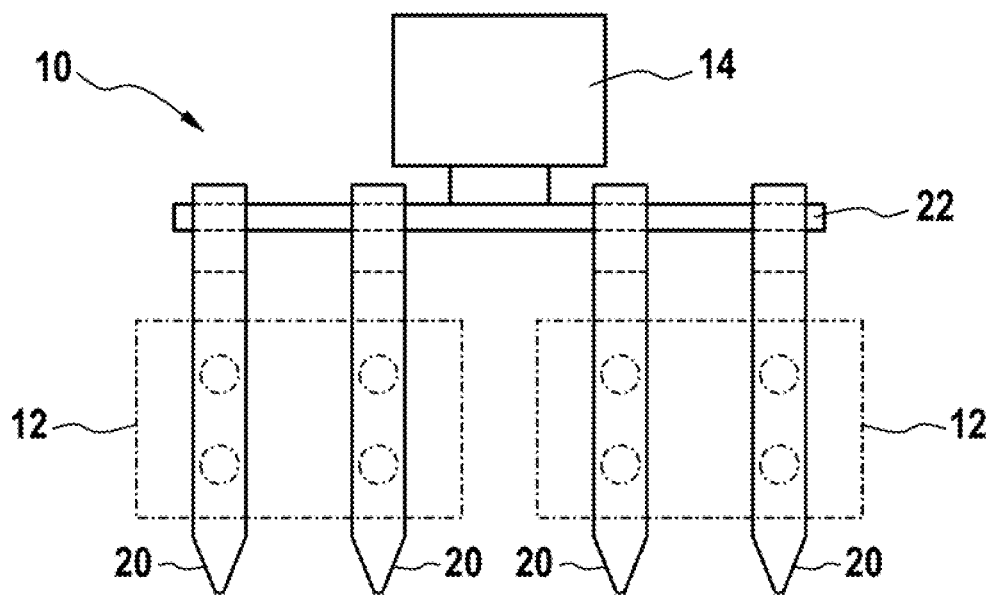
FIG. 5 is a top view showing a plane of the support device according to FIG. 2 with a greater number of tines.

In this respect, the views in FIG. 4 and FIG. 5 show different configurations of a plane of the support device 10 formed with at least two tines 20 in each case in a top view of the support device 10. In the situation shown in FIG. 4, compared to the view in FIG. 2, a longer crossbeam 22 is mounted on the column 14. A distance needed for a comparatively wide medical apparatus 12 can therefore be set between the tines 20, which are adjustable, especially movable, in their position along the crossbeam 22. In the situation shown in FIG. 5, two pairs of tines 20 are mounted on a crossbeam 22, so that two medical apparatuses 12 can be placed in the same plane of the support device 10. With additional tines 20, more than two medical apparatuses 12 can also be placed in one plane.

Figure 6:
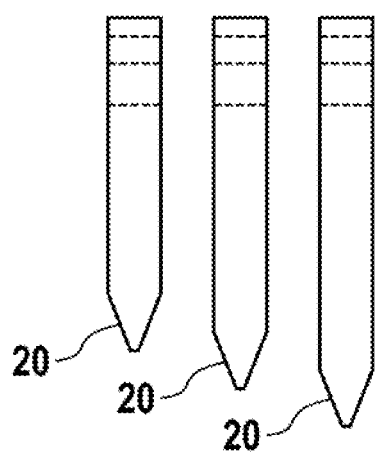
FIG. 6 is a schematic view showing tines of different lengths as well as crossbeams of different lengths.
Figure 6:
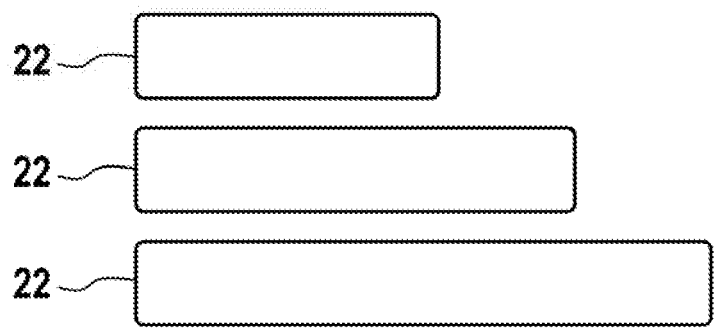

Of course, the configurations shown in the views in FIG. 2, FIG. 4 and FIG. 5 are only to be understood as examples and a variety of other configurations are possible with the support device 10 proposed here and functioning as a bracket system for medical apparatuses 12, wherein the ability of very extensively influencing the configuration of the support device 10 precisely represents an essential advantage of the innovation proposed here and is the basis of the flexibility of the bracket system. In this respect, the view in FIG. 6 shows—only as an example—tines 20 of different lengths and crossbeams 22 of different lengths. A modular support device 10, which can be adapted to nearly any application situation by mounting the particularly needed crossbeam 22 on the column 14 and by mounting the particularly needed tine 20 on the crossbeam or a crossbeam 22, is obtained with a number of different tines 20 and different crossbeams 22.

Figure 7:
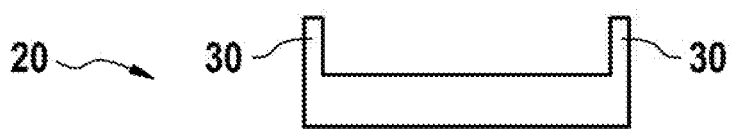
FIG. 7 is an end view showing a special embodiment of a tine with lateral limitations in an area of the support section thereof.
Figure 8:
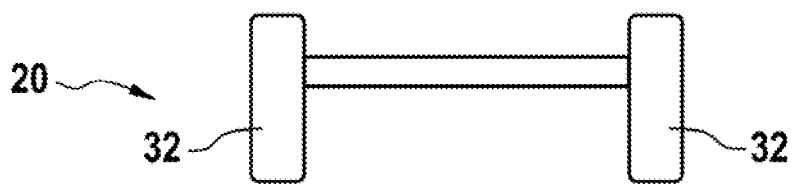
FIG. 8 is an end view showing another special embodiment of a tine with lateral limitations in an area of the support section thereof.

Finally, the views in FIG. 7 and FIG. 8 show special embodiments of a tine 20 in the area of the support section 24 thereof. In each case, a cross section through the support section 24 of the tine 20 is shown. As can be seen, the surface of the support section 24 is limited on both sides.

In the embodiment according to FIG. 7, lateral limitations 30, especially connected in one piece with the rest of the material of the tine 20, in case of an impact on a medical apparatus 12 placed in the support device 10, prevent the support feet thereof from sliding down from the comparatively small shelf space of a tine 20 because of the impact.

In the embodiment of FIG. 8, standard rails 32 function as lateral limitations 32 for the mounting (attaching, clipping on, screwing on, etc.) of medical apparatuses 12. Insofar as a medical apparatus 12 likewise stands on such a tine 20, the standard rails 32 likewise function as protection against a slipping out or even falling out of the medical apparatus 12 from the support device 10.

Some of the prominent aspects of the specification submitted here can thus be briefly summarized as follows: A support device 10 functioning as a bracket system for medical apparatuses 12 is indicated, which support device 10 comprises a central vertical or at least essentially vertical column 14 in a manner known, in principal, and is characterized by at least one tine 20, optionally two or more tines 20, which is/are oriented obliquely to a crossbeam 22 mounted on the on the column 14.

While specific embodiments of the invention have been shown and described in detail to illustrate the application of the principles of the invention, it will be understood that the invention may be embodied otherwise without departing from such principles.

APPENDIX

List of Reference Designations

1 Support device
10 Support device
12 Medical apparatus
14 Column
16 Shelf space
18 (blank)
20 Tine
22 Crossbeam
24 Support section (of a tine)
26 Suspended section (of a tine)
28 Adjusting screw
30 Lateral limitation
32 Standard rail (as lateral limitation)

What is claimed is:

1. A medical apparatus support device for at least one medical apparatus, the medical apparatus support device comprising:

a central vertical or at least essentially central vertical column;

a crossbeam mounted on the column, the crossbeam comprising a first crossbeam surface facing in a direction of the central vertical or at least essentially vertical column and the crossbeam comprising a second crossbeam surface facing in a direction away from the central vertical or at least essentially vertical column, wherein the first crossbeam surface is located opposite the central vertical or at least essentially vertical column; and at least one tine connected to the crossbeam and oriented transversely to the crossbeam, the at least one tine comprising a suspended section providing a connection of the at least one tine to the crossbeam for mounting the at least one tine on the crossbeam by the suspended section, wherein a first portion of the suspended section engages the first crossbeam surface, the first portion of the suspended section being located between the crossbeam and the central vertical or at least essentially vertical column, the suspended section comprising a second portion comprising a second portion surface facing in the direction of the central vertical or at least essentially vertical column, at least a portion of the second portion surface and the first portion of the suspended section defining a space, wherein a portion of the crossbeam is arranged in the space, wherein the connection of the at least one tine to the crossbeam comprises an adjustable connection whereby a position of the tine on the crossbeam is adjustable in an axial direction of the crossbeam, the at least one tine comprising a planar medical apparatus support surface extending from the suspended section to an end of the at least one tine, the planar medical apparatus support surface comprising a medical apparatus contact surface portion configured to be in direct contact with the at least one medical apparatus for supporting the at least one medical apparatus, wherein the planar medical apparatus support surface extends continuously, without interruption, from a position directly adjacent to the second portion of the suspended section to an end of the at least one tine, the second portion of the suspended section being located at a spaced location from the crossbeam, the second portion of the suspended section being free of contact with the crossbeam, wherein the at least one tine is in contact in some sections with a top side of the crossbeam and is indirectly or directly supported on the second crossbeam surface of the crossbeam, the second crossbeam surface being parallel to the central vertical or essentially vertical column, the crossbeam comprising a bottom side, the at least one tine comprising a medical apparatus support section extending continuously, directly from the second portion of the suspended section to the end of the at least one tine, the medical apparatus support section comprising the planar medical apparatus support surface, wherein each and every portion of the medical apparatus support section is located between a first horizontal plane including the top side of the crossbeam and a second horizontal plane including the bottom side of the crossbeam.

2. A medical apparatus support device in accordance with claim 1, wherein the at least one tine comprises at least two tines oriented perpendicular to the crossbeam and aligned parallel to one another, the at least two tines being located at a spaced location from one another such that the at least one medical apparatus bridges a space between the at least two tines, the suspended section comprising an uppermost surface located at a position above the crossbeam, the uppermost surface extending continuously from a position located on one side of the crossbeam to another position located on another side of the crossbeam, wherein the planar medical apparatus support surface is located at a position below the uppermost surface.

3. A medical apparatus support device in accordance with claim 2, wherein the connection of each of the at least two tines to the crossbeam comprises an adjustable connection to adjust a position of each tine on the crossbeam in an axial direction of the crossbeam whereby a distance between two adjacent tines mounted on the crossbeam is adjustable.

4. A medical apparatus support device in accordance with claim 1, wherein the connection of the at least one tine to the crossbeam comprises a detachable connection, whereby the at least one tine is detachably connected to the crossbeam, the at least one tine comprising a planar tine surface parallel to the planar medical apparatus support surface, the planar tine surface extending from the suspended section to the end of the at least one tine, the first portion of the suspended section and the central vertical or at least essentially central vertical column defining a space, wherein no structure is provided between the first portion of the suspended section and the central vertical or at least essentially central vertical column.

5. A medical apparatus support device in accordance with claim 1, wherein the crossbeam on the column comprises a detachable mount, whereby the crossbeam can be detachably connected to the central vertical or at least essentially central vertical column, the first portion of the suspended section being located on one side of the crossbeam and the second portion of the suspended section being located on another side of the crossbeam, the suspended section comprising a third portion extending above the crossbeam, the first portion of the suspended section being connected to the second portion of the suspended section via the third portion, the crossbeam comprising a third crossbeam surface extending between the first crossbeam surface and the second crossbeam surface, the suspended section only being in contact with a portion of the third crossbeam surface and a portion of the first crossbeam surface.

6. A medical apparatus support device in accordance with claim 5, further comprising at least another crossbeam to provide a plurality of crossbeams, and at least another tine to provide a plurality of tines, each of the plurality of tines being configured to be detachably connected to only a single one of the crossbeams, the planar medical apparatus support surface being located at a first height relative to a lower portion of the central vertical or at least essentially central vertical column, the third portion of the suspended section being located at a second height relative to the lower portion of the central vertical or at least essentially central vertical column, the first height being less than the second height, wherein:
 the plurality of crossbeams are of different lengths; or
 the plurality of tines are of different lengths; or
 the plurality of crossbeams are of different lengths and the plurality of tines are of different lengths.

7. A medical apparatus support device in accordance with claim 5, further comprising at least another crossbeam to provide a plurality of crossbeams, and at least another tine to provide a plurality of tines, each of the plurality of tines being configured to be detachably connected to only a single one of the crossbeams, wherein:
 the plurality of crossbeams are of different lengths; or
 the plurality of tines are of different lengths; or
 the plurality of crossbeams are of different lengths and the plurality of tines are of different lengths.

8. A medical apparatus support device in accordance with claim 7, wherein the crossbeam has a rectangular cross section and a largest longitudinal axis of a cross-sectional area of the crossbeam, in a state of the crossbeam mounted on the column, is oriented vertically or at least essentially vertically.

9. A medical apparatus support device in accordance with claim 1, wherein the tine comprises a support section and an adjustment means for adjusting an inclination of the support section of the tine relative to a horizontal plane, the adjustment means engaging the crossbeam, wherein the at least one tine is supported via only one said crossbeam.

10. A medical apparatus support device in accordance with claim 1, wherein the crossbeam has a rectangular cross section and a largest longitudinal axis of a cross-sectional area of the crossbeam, in a state of the crossbeam mounted on the column, is oriented vertically or at least essentially vertically.

11. A medical apparatus support device in accordance with claim 1, wherein the at least one tine has lateral limitations, the suspended section comprising an uppermost surface located at a position above the crossbeam, the uppermost surface extending continuously from a position located on one side of the crossbeam to another position located on another side of the crossbeam, wherein the planar medical apparatus support surface being located at a spaced location from the uppermost surface.

12. A medical apparatus support device in accordance with claim 11, wherein the lateral limitations each comprise a rail.

13. A medical apparatus flexible bracket system comprising:
 a medical apparatus comprising a medical apparatus longitudinal axis;
 a central vertically extending column;
 a crossbeam mounted on the column, the crossbeam comprising a crossbeam longitudinal axis, the medical apparatus longitudinal axis being parallel to the crossbeam longitudinal axis, the crossbeam defining opposed clamping surfaces, one of the opposed clamping surfaces facing in a direction of the central vertically extending column, wherein the one of the opposed clamping surfaces is located opposite the central vertically extending column;

a plurality of tines oriented transversely to the crossbeam and aligned essentially parallel to one another, wherein each of the plurality of tines is connected to the crossbeam clamping surfaces by an adjustable and detachable connection whereby a position of each tine on the crossbeam is adjustable in an axial direction of the crossbeam and whereby each tine is detachably connected to the crossbeam, each of the tines comprising a suspended section providing a connection of a respective tine to the crossbeam for mounting the respective tine on the crossbeam by the suspended section, wherein a first portion of the suspended section engages the one of the opposed clamping surfaces, the first portion of the suspended section being located between the crossbeam and the central vertically extending column, the suspended section comprising a second portion comprising a second portion surface facing in 0 the direction of the central vertically extending column, at least a portion of the second portion surface and the first portion of the suspended section defining a crossbeam space, wherein a portion of the crossbeam is arranged in the crossbeam space, one of the plurality of tines being located at a spaced location from another one of the plurality of tines, wherein the one of the plurality of tines and the another one of the plurality of tines define a space, the medical apparatus bridging the space between the one of the plurality of tines and the another one of the plurality of tines, each of the one of the plurality of tines and the another one of the plurality of tines comprising a medical apparatus support section, the medical apparatus support section comprising a planar medical support section surface having a medical apparatus contact surface portion, the medical apparatus contact surface portion being in direct contact with the medical apparatus, wherein a portion of the planar medical support section surface extends continuously, without interruption, from a position directly adjacent to the second portion of the suspended section to an end of one of the tines, the second portion of the suspended section being located at a spaced location from the crossbeam, wherein the second portion does not contact the crossbeam, wherein each of the tines is in contact in some sections with a top side of the crossbeam and is indirectly or directly supported on another one of the opposed clamping surfaces, the another one of the opposed clamping surfaces being parallel to the central vertical or essentially vertical column, the crossbeam comprising a bottom side, each of the medical apparatus support sections extending continuously, directly from the second portion of the suspended section to the end of a respective one of the plurality of tines, wherein each and every portion of the medical apparatus support section is located between a first horizontal plane including the top side of the crossbeam and a second horizontal plane including the bottom side of the crossbeam.

14. A medical apparatus flexible bracket system in accordance with claim 13, wherein the crossbeam on the column comprises a detachable mount, whereby the crossbeam can be detachably connected to the central column, the first portion of the suspended section being located on one side of the crossbeam and the second portion of the suspended section being located on another side of the crossbeam, the suspended section comprising a third portion extending above the crossbeam, the first portion of the suspended section being connected to the second portion of the suspended section via the third portion, wherein the crossbeam is only in contact with a portion of the third portion of the suspended section and the first portion of the suspended section, the third portion comprising an uppermost surface extending above the crossbeam, the uppermost surface extending continuously from a position located on one side of the crossbeam to another position located on another side of the crossbeam, wherein the portion of the planar medical support section surface is located at a position below the uppermost surface.

15. A medical apparatus flexible bracket system in accordance with claim 14, further comprising at least another crossbeam to provide a plurality of crossbeams, the plurality of tines being located at a spaced location from the another crossbeams, the planar medical support section surface being located at a first height relative to a lower portion of the central vertically extending column, the third portion of the suspended section being located at a second height relative to the lower portion of the central vertically extending column, the first height being less than the second height, wherein:
  the plurality of crossbeams are of different lengths; or
  the plurality of tines are of different lengths; or
  the plurality of crossbeams are of different lengths and the plurality of tines are of different lengths.

16. A medical apparatus flexible bracket system in accordance with claim 14, wherein each tine is supported via only one said crossbeam, the one of the plurality of tines being located at a spaced location from another one of the plurality of tines in a direction parallel to the medical apparatus longitudinal axis.

17. A medical apparatus flexible bracket system in accordance with claim 16, wherein an adjustment means for adjusting an inclination of the medical apparatus support section of the tine relative to a horizontal plane, the adjustment means being in direct contact with the crossbeam.

18. A medical apparatus flexible bracket system in accordance with claim 14, wherein each tine has lateral limitations, the first portion of the suspended section and the central vertically extending column defining a space, wherein no structure is provided between the first portion of the suspended section and the central vertically extending column.

\* \* \* \* \*